United States Patent [19]

Powell

[11] 4,256,403
[45] Mar. 17, 1981

[54] COMBINATION WATER CONTAMINANT AND FUEL DENSITY DETECTOR

[75] Inventor: Frederic D. Powell, Middlebury, Vt.

[73] Assignee: Simmonds Precision Products, Inc., Tarrytown, N.Y.

[21] Appl. No.: 23,513

[22] Filed: Mar. 23, 1979

[51] Int. Cl.³ .................... G01N 21/00; G01N 21/41; G01N 21/84

[52] U.S. Cl. ........................... 356/73; 73/293; 250/577; 356/133

[58] Field of Search ............ 356/73, 133, 136; 250/573, 577, 578; 340/619; 73/32 R, 293

[56] References Cited

U.S. PATENT DOCUMENTS

| | | | |
|---|---|---|---|
| 2,976,763 | 3/1961 | McKeag | 250/577 |
| 3,683,196 | 8/1972 | Obenhaus | 250/577 |
| 3,932,038 | 1/1976 | Schweizer et al. | 356/133 |

FOREIGN PATENT DOCUMENTS

| | | | |
|---|---|---|---|
| 1301082 | 12/1972 | United Kingdom | 356/136 |
| 2014724 | 8/1979 | United Kingdom | 73/32 R |

*Primary Examiner*—John K. Corbin
*Assistant Examiner*—Wm. H. Punter

*Attorney, Agent, or Firm*—Edwin E. Greigg

[57] ABSTRACT

A device for detecting the presence of contaminating water in a fuel tank as well as for measuring the density of the fuel in the tank which includes an elongated body of optical material arranged to be mounted in a fuel tank in a vertically extending position, one side face of the body forming an interface with the fluid in the tank, and a plurality of light sensors on the opposite face of the body arranged in spaced-apart relationship, together with light-emitting means at the bottom of the body which emit a divergent group of rays of successively increasing angles of incidence upwardly so that those rays exceeding the critical angle at the interface for a fuel of a specific index of refraction are reflected to illuminate those sensors corresponding to the rays exceeding the critical angle to thereby provide a detected output representing the density of the fluid, the light-emitting means providing a second group of rays striking the lower portion of the interface which are reflected when water is present to illuminate another light sensor for indicating such water presence. This invention relates to a fuel detector and more particularly to a detector for indicating both fuel density and the presence of water in a fuel tank.

16 Claims, 4 Drawing Figures

COMBINATION WATER CONTAMINANT AND FUEL DENSITY DETECTOR

BACKGROUND OF THE INVENTION

The measurement of the density of a fluid is essential today in many areas, one of the most significant of which is the measurement of the density of fuel in a fuel tank such as a tank incoporated in an aircraft. In addition, it is highly desirable that in addition to a measurement of density an indication of the presence of water in the tank should be obtained. Many devices have been proposed in the past by means of which a measurement of fuel density has been obtained. A common type of such a device utilizes a light-transmitting body of optical material such as glass or the like having various configurations so as to provide reflective and refractive surfaces by means of which light transmitted through the body is altered from its normal path according to the indices of refraction between the optical material of the light-transmitting body and the fluid in which the body is immersed. However, such present-day devices are characterized by many limitations, not the least of which are their complexity and attendant high cost. In addition, such present-day devices for the measurement of density utilize components which must be waterproofed and are provided with surfaces which are adversely affected by bacterial growth in the fluid such as fuel, so that the readings obtained with the device lack the desired degree of accuracy required for proper functioning.

OBJECTS AND SUMMARY OF THE INVENTION

Accordingly, a primary object of this invention is to provide a new and novel detector for measuring the density of a fluid such as fuel which is of extremely simple construction and which is composed of a minimum of parts.

Another object of this invention is to provide a new and novel fuel density measuring device which also provides an indication of the presence of water in the fuel.

Still another object of this invention is to provide a new and novel combination water contaminant and fuel density measuring device which not only indicates the presence of water in the fuel but produces highly accurate fuel density measurements throughout a wide range.

Still another object of this invention is to provide a new and novel combination water contaminant and fuel density detector which does not depend on the optical properties of the fuel other than the index of refraction, wherein the light rays used to measure fluid density do not pass through the fuel, so that the device is insensitive to foreign matter in the fuel such as dirt due to bacterial growth and the like.

Other related objects of the invention are accomplished by the provision of a longitudinally extending light-transmitting body adapted to be disposed within a fuel tank in an upstanding position, a substantially vertically extending side face on the body forming an interface with the fluid in the tank. Light-emitting means are provided on the bottom end of the body for transmitting emitted light angularly upward through the body in a group of divergent rays at upwardly increasing angles of incidence to strike the interface, those rays whose angle of incidence exceeds the critical angle at the interface determined by the index of refraction of the fuel being reflected onto a plurality of vertically spaced light sensors mounted on the opposite side face of the body together with detection means connected to the light sensors for sensing the dark-light boundary between the sensors for producing a signal corresponding to the index of refraction and therefore the density of the fuel.

The invention will be better understood as well as further objects and advantages thereof become more apparent from the ensuing detailed description of a preferred embodiment taken in conjunction with the drawing.

BRIEF DESRIPTION OF THE DRAWINGS

DESCRIPTION OF THE PREFERRED EMBODIMENT

Figure 1:
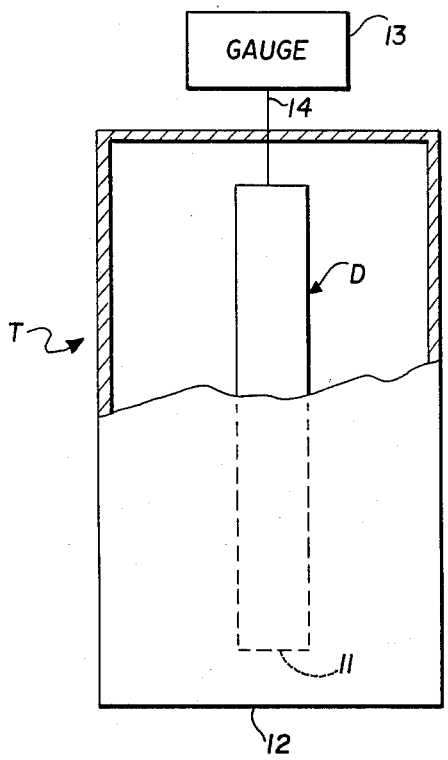
FIG. 1 is a side elevation view partially broken away showing the detector of the invention in an installed position.

Referring now to FIG. 1, there is shown a tank T such as the fuel tank of an aircraft for containing a fluid such as fuel and in the interior of which is mounted a detector constructed in accordance with the invention and designated generally by the letter D. As shown in FIG. 1, the detector D is disposed within the interior of the tank T in an upstanding position with the bottom end 11 of the detector D positioned closely adjacent the bottom wall 12 of the tank T. As will be explained hereinafter, the detector D is arranged to be connected to a gauge 13 of any suitable construction by means of conductors 14, the gauge 13 being arranged to indicate both the density of the fuel within the tank T and the presence of water in the tank.

Figure 2:
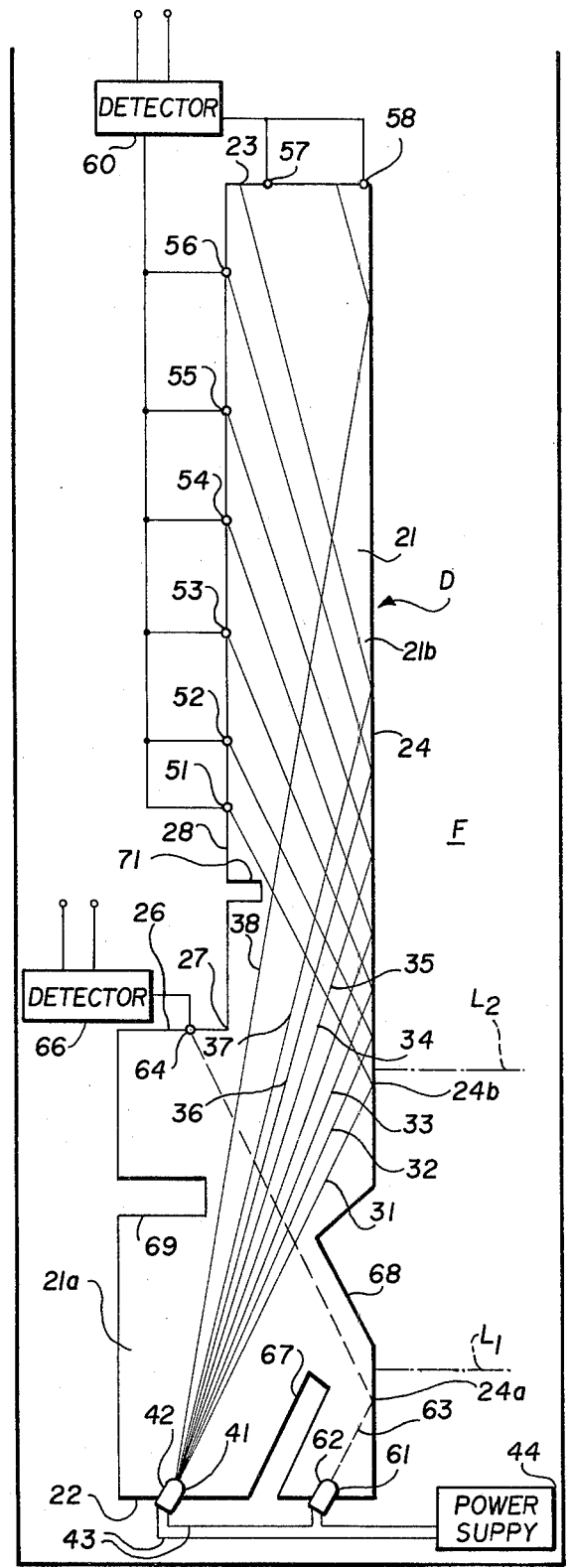
FIG. 2 is an enlarged view of the detector of the invention.

Referring now to FIG. 2, there is shown the detector D of the invention, which includes a longitudinally extending body 21 of light-transmitting material such as glass or other optical material such as plastic which is arranged to be immersed in a substantially vertical position in the fuel tank T as shown in FIG. 1. The body 21 includes a bottom end 22 and a top end 23 with one vertically extending side 24 forming an interface with the fluid F in the tank T. In the preferred embodiment, the body 21 includes a lower portion 21a and a necked-down upper portion 21b forming a horizontally extending ledge 26 and a corner 27 on the side face 28 of the body opposite the interface 24.

Light-emitting means are provided on the bottom end 22 of the body 21 for transmitting emitted light to the interface 24 in the form of a group of divergent rays 31–38 in angularly disposed light emission paths. It should be understood that rays 31–38 are representative of such a group of rays, a larger or smaller number of rays being within the scope of the invention in accordance with the specific embodiment desired. More specifically, the light-emitting means includes a lamp 41 preferably mounted within a recess 42 in the bottom end 22 and connected by means of conductors 43 to an associated source of power 44.

Figure 3:
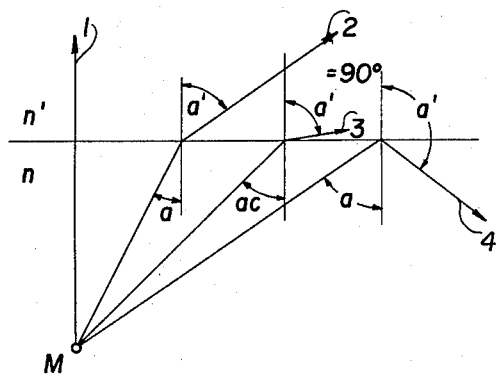
FIG. 3 is a sketch illustrating the optical principles on which the invention is based.

It should be understood at the outset that the principles of the invention are illustrated in FIG. 3 by four monochromatic rays 1, 2, 3 and 4 shown diverging from a common point M in a medium of refractive index n and striking the surface of a second medium of refractive index n' where n>n'. From Snell's Law, sine-(a)'=n/n' sine (a), where a is the angle of incidence ad a' is the angle of refraction. Since n/n' is greater than unity, sine (a)' larger than sine (a) and equals unity (a'=90°) for some angle (a)less than 90°. This is illustrated by ray 3 which emerges just grazing the surface at an angle of refraction of 90°. The angle of incidence for which the refractive ray emerges tangent to the surface is called the critical angle, and is designated by $a_c$ in FIG. 3. If the angle of incidence is greater than the critical angle, the sine of the angle of refraction, as computed by Snell's Law, is greater than unity. This may be interpreted to mean that for $a > a_c$, the ray does not pass into the next medium but is totally internally reflected at the boundary surface. Total internal reflection, accordingly, can occur only when a ray is incident on the surface of a medium whose index is smaller than that of the medium in which the ray is traveling.

In accordance with the principles referred to above, the rays 31–38 have successively increasing angles of incidence upwardly with respect to the interface 24 and will be reflected or refracted in accordance with Snell's Law, the angle of incidence of the light on the interface 24 and the index of refraction of the fluid F.

The detector D also includes a plurality of vertically spaced light sensors 51–56 suitably mounted on the opposite side face 28 of the body 21, each of the light sensors 51–56 being arranged in optical communication with the light reflection paths of the respective one of said rays. More specifically, the light reflection paths of rays 31–36 terminate on light sensors 51–56, which may be photodiodes, phototransistors or the like, which respond in the conventional manner to the reflected rays. At least one light sensor, preferably two light sensors 57, 58, are also mounted on the top end 23 of the body 21 in the light reflection paths of rays 37, 38, it being understood that it is within the scope of the invention to provide any suitable number of light sensors.

In accordance with the principles set forth with respect to FIG. 3, the rays 31–38 whose angle of incidence exceeds the critical angle corresponding to the index of refraction of the fluid F in accordance with Snell's Law are reflected and therefore illuminate the respective light sensor. Conversely, the light sensor or sensors remaining dark are not responsive, as the rays whose angle of incidence is below the critical angle are refracted into the fuel F. As will be explained hereinafter, detector means are connected to each of the sensors 51–58 for detecting the dark-light boundary between the responsive and non-responsive sensors to produce an output signal corresponding to the index of refraction and therefore the density of the fluid F.

The light-emitting means also includes another lamp 61 suitably mounted in the bottom end 22 of the body 21 in a recess 62 and connected by means of conductors 43 to the power supply 44 similar to lamp 41. The lamp 61 transmits an angularly disposed supplemental ray 63 having a terminus on the interface 24 as shown in FIG. 2. A supplemental light sensor 64 is disposed on the opposite side face 28 of the body 21, preferably on the ledge 26, in optical communication with the light reflection path of the supplemental ray 63. The supplemental ray 63 has an angle of incidence corresponding to at least the critical angle of water, whereby the supplemental ray is reflected by the presence of water at the supplemental ray terminus on the lower portion of the interface 24, as indicated by the level $L_1$, so that the supplemental ray 63 is reflected, illuminating the sensor 64, indicating the presence of water at least at a level above the terminus of the ray 63. A detector means such as a detector 66 is connected to the sensor 64 which may be a photodiode or a phototransistor or the like so that when the supplemental sensor 64 is illuminated the detector 66 produces an output signal indicative of the presence of water in the fuel tank T.

Means are provided for separating the light emission and light reflection paths of the group of rays 31–38 from the light emission and light reflection paths of the supplemental ray 63. More specifically, an upwardly directed, angularly disposed notch 67 is provided in the bottom end 22 of the body 21 between the lamps 41 and 61, so that light in the light emission path of the supplemental ray 63 is occluded from striking any of the light sensors 51–58. Additionally, a notch 68 having a non-reflective surface is formed within the interface 24 adjacent the body bottom end 22, thereby occluding light in the light reflection path of the supplemental ray 63 from the light sensors 51–58.

To insure that light in the light emission paths of the rays 31–38 does not illuminate the supplemental sensor 64, another inwardly directed notch 69 having a non-reflective surface is provided in the opposite side face of the body 21, thereby occluding light transmitted by the lamp 41 from the supplemental sensor 64. Where light sensors 57, 58 are provided on the body top end 23, it is also necessary to occlude light from the lamp 41 in the light emission paths from illuminating sensors 57, 58. Therefore, although notch 69 may provide some occlusion of such light, preferably an inwardly directed notch 71 having a non-reflective surface is provided in the opposite side face 28 in the necked-down portion 21b of the body 21, so that all of the light reflection paths of the rays from lamp 41 terminate on the interface 24. It should be understood that some occlusion may also be provided by the corner 27.

In the operation of the invention, the angle of incidence of the supplemental ray 63 at point 24a on the interface 24 is 63°. If fuel is present at point 24a, supplemental ray 63 will be refracted into the fuel. However, if water is present at point 24a, the supplemental ray 63 is totally reflected according to Snell's Law and illuminates supplemental sensor 64. Thus, sensor 64 responds if, and only if, a fluid with index equal to or less than that of water is present at point 24a. Thus, sensor 64 is a water detector.

With respect to the group of rays from lamp 41, the lowermost ray 31 is incident on interface 24 at point 24b parallel to the supplemental ray 63 and therefore having an angle of incidence of 63°. If there is fuel at point 24b, ray 31 will be refracted and sensor 51 will not be illuminated. However, if there is water at point 24b the ray 31 will be reflected, illuminating sensor 51, so that sensor 51 is also a water detector.

In the typical operation, with water absent from the fuel tank or at least below the level at point 24a, ray 31 refracts into all fuels. If we assume that a low-density, low-index-of-refraction fuel having an index of refraction of 1.36 is present, rays 32–38 will be reflected so that sensors 52–58 are illuminated, with sensor 51 remaining dark. With a fuel of a somewhat higher index of refraction, such as 1.40, then rays 31, 32 are refracted, but rays 33–38 are reflected, illuminating sensors 53–58, with sensors 51, 52 remaining dark. As the index of refraction of the fuel increases, succeeding sensors become dark so that the dark-light boundary between sensors indicates the index of refraction of the fuel. Those sensors responding to illumination are therefore detected in the detector 60 to produce an output signal which reflects the fuel index of refraction from which the density of the fuel may be computed.

Figure 4:
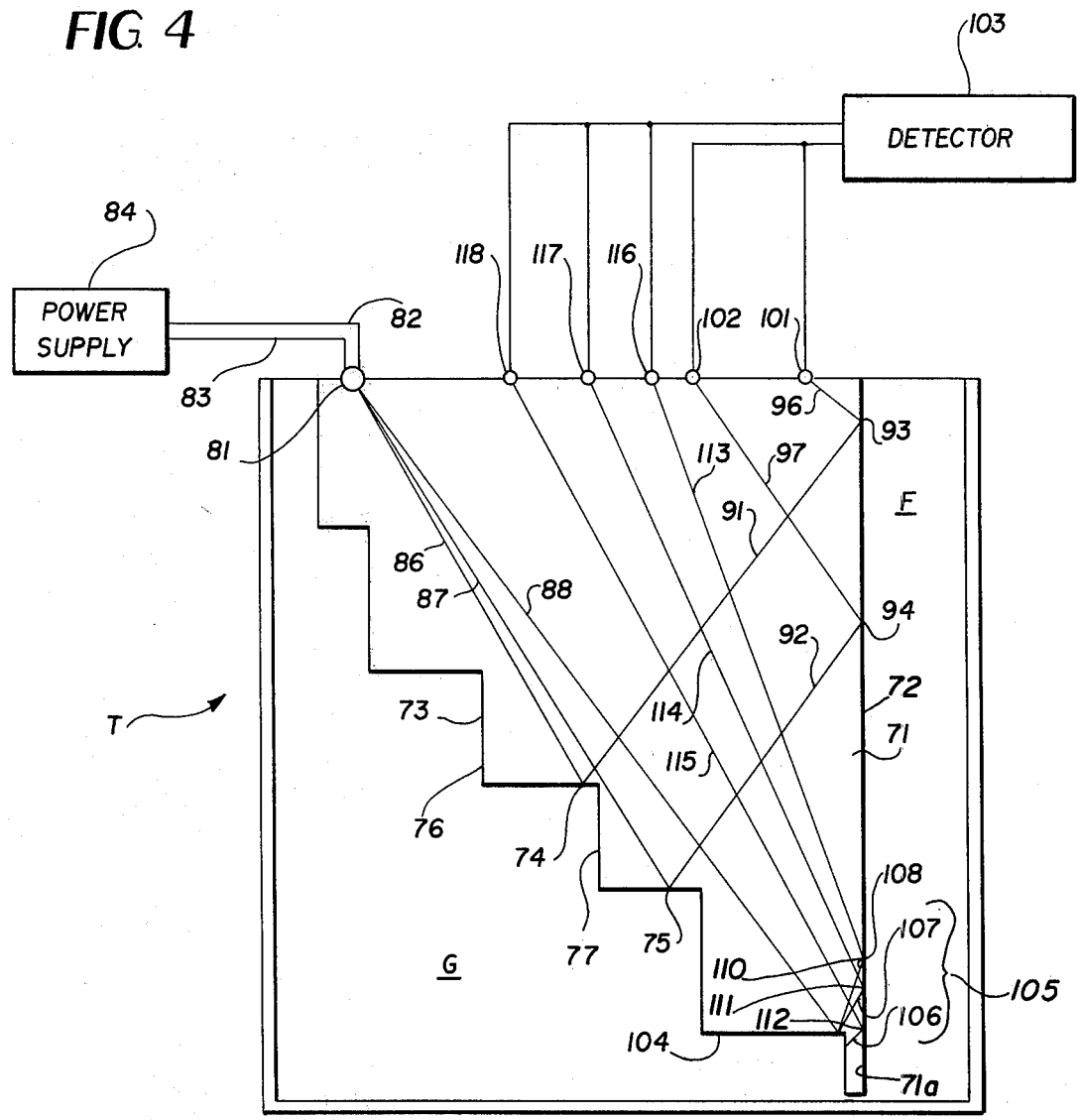
FIG. 4 is a side elevation view of another embodiment of the invention.

Referring now to FIG. 4 there is shown another embodiment of the invention which includes a light-transmitting body 71 arranged to be mounted in a fuel tank as described above with reference to the embodiment of FIGS. 1,2. The body 71 is similarly formed of a suitable material of optical quality such as plastic or the like, and is preferably of triangular configuration having an apex 71a which when the body 71 is mounted in the fuel tank is disposed adjacent the bottom of the tank.

The body 71 includes a substantially vertically extending side face 72 forming an interface or reflect-refract surface in contact with the fuel f. The interface 72 may also be curved if desired in accordance with the geometry with the reflect-refract requirement but a flat surface is preferred primarily on the basis that polishing such a surface if necessary is facilitated if the surface 72 is flat. It should be understood that interface 72 is merely polished and is not silvered.

The body 71 also includes a marginal edge portion 73 extending oppositely the interface 72 and in angularly disposed relationship therewith. The marginal edge portion 73 is preferably of saw-toothed configuration so as to define a plurality of reflected areas such as areas 74, 75 with intervening areas such as areas 76, 77 which may be frosted or merely oriented so as to be shadowed from the light striking reflective surfaces 74, 75.

Light transmitting means as a single illuminating light 81 is positioned on the body 71 preferably on the upper portion of the body within the body upper edge 82 adjacent the marginal edge portion 73. The light 81 is connected by conductors 83 to a suitable power supply 84. Thus, light from the lamp 81 is transmitted downwardly within the body 71 adjacent the marginal edge portion 73 in a plurality of rays as illustrated by rays 86, 87 and 88.

Some of the rays such as rays 86, 87 from lamp 81 which strike reflective areas 74, 75 respectively, are reflected along paths 91, 92, respectively, and impinge internally on the interface 72 at a first group of selected locations 93, 94 respectively. In accordance with Snell's Law as explained above with respect to the embodiment of FIGS. 1, 2 the reflected rays from reflective areas 74, 75 impinging at locations 93, 94 respectively, are either reflected within the body 71 or refracted to the fluid f if fluid is present in the tank at locations 93, 94 or reflected within the body 71 along paths 96, 97 respectively if fluid is absent at locations 93, 94. For this action to occur it is required that the angle of incidence of the rays in the light reflective path 91, 12 have an angle of incidence with respect to the interface 72 within the range of approximately 60° to 75° to thereby distinguish between air and fuel at the interface 72.

In order to sense the reflected rays 96, 97 a plurality of light sensors such as light sensors 101, 102 are provided on the body 71 suitably connected to a detector 103, the light sensors 101, 102 being in optical communication with the reflected rays 96, 97, respectively. Thus, a reflected ray from the interface 72 such as ray 96 striking sensor 102 indicated the absence of fluid at location 93 and responds accordingly, which response is detected by the detector 103 as explained above.

It should be understood that the light sensors 101, 102 may be of any suitable type such as analog detectors or discrete optical detectors.

The marginal edge portions 73 of the body 71 also preferably include an arcuate mirror-surface 104 adjacent the apex 71a of body 71 which is arranged to reflect rays such as ray 88 emanating from the light source 81. The reflector 104 is arranged to reflect rays such as ray 88 in a plurality of reflective paths 106, 107, 108 onto a second group of spaced-apart locations on the lower portion of the interface 72 identified by the numerals 110, 111 and 112. The reflected rays traveling in the light reflective paths 106–108 from locations 110–112 are either reflected or refracted in accordance with Snell's Law as explained above with reference to the embodiment of FIGS. 1, 2 within the interior of the body 71 in a group of light reflective paths 113, 114, 115 so as to strike a second group of sensors 116, 117, 118, respectively. The rays 106–108 are reflected from the mirror-surface or reflector 104 so as to impinge on the region 105 of the interface 72 wherein which the locations 110–112 are positioned at angles of incidence ranging from 62° to 77°. The ray incident at 62° will refract if there is water present within the region 105 and will refract into the fluid f if the fluid is oil in accordance with Snell's Law. Rays 106–108 having angles of incidence ranging between 68° to 77° will reflect within the body 72 if the index refraction of fuel f is low representing a fuel of low density and will refract into the fuel f for higher fuel densities. As in the embodiment of FIGS. 1, 2 the sensors 116–118 respond to the reflected rays 113–115, respectively, the response of which being detected by the detector 103 as in the embodiment of FIGS. 1, 2.

It should be understood that other embodiments are contemplated within the scope of the invention such as the use of a plurality of internal reflecting surfaces and an interface or reflect-refract surface as well as variations in the locatons of the light-emitting means and the light sensors on the light-transmitting body.

The foregoing relates to a preferred embodiment of the invention, it being understood that other embodiments and variants thereof are possible within the spirit and scope of the invention, the latter being defined by the appended claims.

What is claimed and desired to be secured by Letters Patent of the United States is:

1. A water/fuel density detector for a fuel tank or the like comprising, in combination, a longitudinally extending light-transmitting body adapted to be disposed within a fuel tank in an upstanding position with the bottom end of said body adjacent the bottom of said tank, said body having a substantially vertically extending side face forming an interface with the fluid in said tank, light-emitting means on the bottom end of said body for transmitting emitted light to said interface in the form of a group of divergent rays in angularly disposed light emission paths, said rays having successively increasing angles of incidence upwardly with respect to said interface, a plurality of vertically spaced light sensors mounted on an opposite side face of said body, each of said light sensors being arranged in optical communication with the light reflection paths of a respective one of said rays, said sensors being responsive to the reflected rays whose angle of incidence exceeds the critical angle corresponding to the index of refraction of said fluid in accordance with Snell's Law and non-responsive to said rays whose angle of incidence is below said critical angle and are thereby refracted into said fluid, detection means connected to said light sensors for detecting the dark-light boundary between said responsive and non-responsive sensors to produce an output signal corresponding to the index of refraction and therefore to the density of said fluid said light-emitting means being arranged to transmit an angularly disposed supplemental ray of emitted light having a terminus on said interface adjacent the bottom end of said body, said supplemental ray having an angle of incidence corresponding to at least the critical angle of water whereby said supplemental ray is reflected by the presence of water at said supplemental ray terminus, and a supplemental light sensor on said body opposite said side face arranged in optical communication with the reflection path of said supplemental ray for response to said reflected supplemental ray and wherein said detection means is connected to said supplemental light sensor for detecting the response of said supplemental light sensor to provide an output signal indicative of the presence of water at a level on said interface corresponding to said supplemental ray terminus.

2. A water/fuel density detector in accordance with claim 1 wherein the angle of incidence of the lowermost ray in said group of rays is at at least the critical angle corresponding to the index of refraction for water as said fluid whereby said lowermost ray is reflected by the presence of water at a level on said interface coincident with the terminus of said lowermost ray on said interface for response by the light sensor in the light reflection path of said lowermost ray.

3. A water/fuel density detector in accordance with a claim 1 including means for separating the light emission and the light reflection paths of said group of rays from the light emission and the light reflection paths of said supplemental ray.

4. A water/fuel density detector in accordance with claim 1 wherein said plurality of sensors include at least one light sensor on the upper end of said body in optical communication with the light reflection path of at least the uppermost ray in said group of rays.

5. A water/fuel density detector in accordance with claim 1 wherein said light-emitting means includes a pair of lamps mounted on said body bottom end, the output of one of said lamps providing said group of divergent rays and the output of the other of said lamps providing said supplemental ray and means for connecting said pair of lamps to an associated source of electrical power.

6. A water/fuel density detector in accordance with claim 5 including an inwardly directed, angularly disposed notch having a non-reflective surface in said body between said pair of lamps for occluding light in said light emission path of said supplemental ray from said plurality of light sensors and an inwardly directed notch having a non-reflective surface in said interface adjacent said body bottom end for occluding light in said light reflecttion path of said supplemental ray from said plurality of light sensors.

7. A water/fuel density detector in accordance with claim 6 including an inwardly directed notch having a non-reflective surface in said body opposite side face for occluding light in said light emission paths of said group of divergent rays from said supplemental light sensor.

8. A water/fuel density detector in accordance with claim 7 wherein said light-transmitting body includes a necked-down upper portion forming a ledge having a corner on said opposite side face and wherein said supplemental light sensor is disposed on said ledge.

9. A water/fuel density detector in accordance with claim 8 including an inwardly directed notch having a non-reflective surface on the opposite side face of said necked-down portion for occluding light in the light emission paths of said group of divergent rays from the upper end of said body.

10. A water/density detector for a fuel tank or the like comprising, in combination, an elongated light-transmitting body adapted to be disposed within a fuel tank in an upstanding position with the lower portion of said body adjacent the bottom of said tank, said body having a side face forming an interface with the fluid in said tank, said body having a plurality of internal reflection areas adjacent a marginal edge of said body, light-emitting means on said body for transmitting emitted light in the form of a group of divergent rays within said body onto said interface in a plurality of regularly disposed light emission paths, a plurality of light sensors mounted on said body in optical communication with the light reflection paths of said rays reflected from said interface within said body, some of said sensors being adapted to respond only to rays reflected from said interface for indicating the absence of fluid at spaced apart locations on said interface from which said rays are reflected, other of said sensors being adapted to respond only to the rays reflected from other locations on said interface in accordance with the density of said fluid at said other locations on said interface, the reflection or refraction of all of said rays impinging on said interface being determined in accordance with Snell's Law and detection means connected to said light sensors for detecting the response of said light sensors to said rays reflected from said interface, said body including said lower portion provided with a plurality of reflective areas and wherein said group of divergent rays from said light-emitting means is directed onto said reflective areas for reflection thereby onto said interface within said body, said rays reflected from some of said reflective areas impinging internally on said interface at first spaed-apart locations for reflection from said interface onto a first group of correspondingly spaced light sensors for indicating the absence of fluid at said first spaced-apart locations, said rays reflected from other of said reflective areas impinging internally on said interface at second spaced-apart locations for reflection onto a second group of correspondingly spaced light sensors for indicating both the presence of water and the fuel index of refraction and therefore the density of the fuel at said second spaced-apart locations.

11. A water/fuel density detector for a fuel tank or the like in accordance with claim 10 wherein said light-emitting means and said plurality of light sensors are positioned on the upper portion of said light-transmitting body.

12. A water/fuel density detector for a fuel tank or the like in accordance with claim 11 wherein said body marginal edge portion extends oppositely from said interface in an angularly disposed relationship therewith, said marginal edge portion being of saw-toothed configuration for defining said reflective areas.

13. A water/fuel density detector for a fuel tank or the like in accordance with claim 12 wherein said body is of triangular shape having an apex disposed adjacent the bottom of said fuel tank.

14. A water/fuel density detector for a fuel tank or the like in accordance with claim 13 wherein said plurality of reflective areas includes a mirror-like surface adjacent said apex for reflecting said another group of said rays onto said second spaced-apart locations and wherein said second spaced-apart locations are positioned on the lower portion of said interface.

15. A water/fuel density detector for a fuel tank or the like in accordance with claim 14 wherein said reflective areas for reflecting said rays onto said first spaced-apart locations are adapted to impinge said reflective rays on said interface at angles of incidence of between approximately 60° to 75°.

16. A water/fuel density detector for a fuel tank or the like in accordance with claim 15 wherein said arcuate, mirror-like surface for reflecting said rays onto said second spaced-apart locations are adapted to impinge said reflective rays on said interface at angles of incidence of between approximately 62° to 77° wherein the ray incident at 62° will reflect upon the presence of water at said interface and will refract upon the presence of oil at said interface and wherein rays having angles of incidence of between 68° to 77° will reflect at low fuel indices of refraction and refract at high indices of refraction.

* * * * *